US005713965A

United States Patent [19]
Foglia et al.

[11] Patent Number: 5,713,965
[45] Date of Patent: Feb. 3, 1998

[54] PRODUCTION OF BIODIESEL, LUBRICANTS AND FUEL AND LUBRICANT ADDITIVES

[75] Inventors: Thomas A. Foglia, Lafayette Hill, Pa.; Lloyd A. Nelson, Highstown, N.J.; William N. Marmer, Fort Washington, Pa.

[73] Assignee: The United States of America as represented by the Secretary of Agriculture, Washington, D.C.

[21] Appl. No.: 631,498

[22] Filed: Apr. 12, 1996

[51] Int. Cl.$^6$ .................. C10L 1/18; C12P 7/62
[52] U.S. Cl. .............. 44/388; 508/463; 435/134; 435/135; 435/198
[58] Field of Search ............... 435/134, 135, 435/198; 44/388

[56] References Cited

U.S. PATENT DOCUMENTS

| | | | |
|---|---|---|---|
| 4,839,287 | 6/1989 | Holmberg et al. | 435/135 |
| 4,956,286 | 9/1990 | Macrae | 435/134 |
| 4,956,287 | 9/1990 | Suzuki et al. | 435/134 |
| 5,061,498 | 10/1991 | Matsuzaki et al. | 435/135 |
| 5,219,744 | 6/1993 | Kurashige et al. | 435/135 |
| 5,316,927 | 5/1994 | Zaks et al. | 435/198 |
| 5,480,787 | 1/1996 | Negishi et al. | 435/135 |
| 5,520,708 | 5/1996 | Johnson et al. | 44/388 |
| 5,525,126 | 6/1996 | Basu et al. | 44/388 |
| 5,578,090 | 11/1996 | Bradin | 44/388 |
| 5,599,358 | 2/1997 | Giavazzi et al. | 44/388 |

OTHER PUBLICATIONS

Ali et al., "Fuel Properties of Tallow and Soybean Oil Esters", *JAOCS*, vol. 72(12), pp. 1557–1564 (1995) (no month).

Richardson et al., "Methyl Esters of Tallow as a Diesel Component", *Proceedings of the Int. Conf. on Energy from Biomass*, Palz, Coombs, Hall (Ed.), pp. 735–743 (1985) (no month).

Natusch et al., "Methyl Esters of Tallow as a Diesel Extender", *Proceedings, XI, Int. Symp. on Alcohol Fuels Tech. Conf.*, 21–25 May 1984, Ottawa, Canada, pp. 2–340–2–346.

Ali et al., "Emissions and Power Characteristics of Diesel Engines . . .", *Bioresource Technology*, vol. 52, pp. 185–195 (1995) (no month).

*Primary Examiner*—Ellen M. McAvoy
*Attorney, Agent, or Firm*—M. Howard Silverstein; John Fado; Janelle S. Graeter

[57] ABSTRACT

A method is described which utilizes lipases to transesterify triglyceride-containing substances and to esterify free fatty acids to alkyl esters using short chain alcohols. The alkyl esters are useful as alternatives or additives to automotive fuels and lubricants. The method is particularly advantageous because it utilizes inexpensive feedstocks such as animal fats, vegetable oils, rendered fats and restaurant grease as substrates.

13 Claims, 2 Drawing Sheets

PRODUCTION OF BIODIESEL, LUBRICANTS AND FUEL AND LUBRICANT ADDITIVES

BACKGROUND OF THE INVENTION

1. Field of the Invention

The use of biofuels as alternatives or additives to currently used petroleum-based automotive fuels and lubricants has been an area of considerable research and investigation, however, several of the most promising sources of biofuels have not proven economically feasible. This invention relates to the process of producing biofuels by lipase-catalyzed transesterification of alcohols utilizing inexpensive feedstocks such as animal fats, vegetable oils, rendered fats and restaurant grease as substrates.

2. Description of the Prior Art

The chemical approach to the synthesis of alkyl esters (Ali and Hanna. 1994. *Bioresource Technology.* vol. 50, pp. 153–163; Freedman et al. 1984. *J. Am. Oil Chem. Soc.* vol. 61, pp. 1638–1643; Lee et al. 1995. *J. Am. Oil Chem. Soc.* vol. 72, pp. 1155–1160) of triglycerides has drawbacks such as difficulties in the recovery of glycerol, the need for removal of salt residue, and the energy-intensive nature of the process. Moreover, chemical synthesis, though efficient in terms of reaction yield and time, suffers from at least two deficiencies: 1) it does not allow for utilizing particular feedstocks, especially those with high free fatty acid content; and 2) it is inefficient with respect to conversion of feedstocks to esters of higher chain alcohols. The use of biocatalysts, on the other hand, does allow for the synthesis of branched alkyl esters, easy recovery of glycerol, and the transesterification of glycerides with high free fatty acid (FFA) content. Moreover, enzymatic methods allow a more facile recovery of glycerol than do chemical methods.

Although a number of studies have reported transesterification and interesterification reactions using lipases (e.g. Zaks and Klibanov. 1985. *Proc. Natl. Acad. Sci.* vol. 82, pp. 3192–3196; Foglia et al. 1993. *J. Am. Oil Chem. Soc.* vol. 70, pp. 281–285; Abraham et al. 1988. *Biotechnology Letters.* vol. 10, pp. 555–558), it is only recently that research has been centered on the use of lipases to produce alkyl esters of fatty acids and alcohols other than methanol. Lipase-catalyzed alcoholysis of sunflower oil (M. Mittelbach. 1990. *J. Am. Oil Chem. Soc.* vol. 67, pp. 168–170), rapeseed oil (Linko et al. 1994. *J. Am. Oil Chem. Soc.* vol. 71, pp. 1411–1414), soybean oil and beef tallow (G. Lazar. 1985. *Fette Seifen Anstrichm.* vol. 87, pp. 394–400) have been reported. These reactions generally, involve the use of primary alcohols with a few scattered reports on transesterifications with secondary alcohols (Shaw et al. 1991. *Enzyme Microb. Technol.* vol. 13, pp. 544–546).

Due to increased environmental consciousness, the use of agriculturally-derived fats and oils as biofuels has become an important area of research. Currently, rapeseed esters are used in Europe (Cvengros and Cvengrosova. 1994. *J. Am. Oil Chem. Soc.* vol. 71, pp. 1349–1352), and palm oil esters are being evaluated in Malaysia (Masjuki and Sapuan. 1995. *J. Am. Oil Chem. Soc.* vol. 72, pp. 609–612) as biodiesel. Soybean oil esters have been proposed as potential diesel fuel alternatives (Goering and Fry. 1984. *J. Am. Oil Chem. Soc.* vol. 61, pp. 1627–1632) in the U.S., thus stimulating considerable research in this area. Methyl and ethyl tallowates have also been tested as diesel fuel substitutes (Dunn and Bagby. 1995. *J. Am. Oil Chem. Soc.* vol. 72, pp. 895–904; Richardson et al. 1985. *Proc. of the International Conference on Energy from Biomass.* vol. 8; Natusch et al. 1984. *Proceedings IV, International Symposium on Alcohol Fuels Technology Conference.* vol. 3, pp. 340–346; Ali et al. 1995. *J. Am. Oil Chem. Soc.* vol. 72, pp. 1557–1564; Ali and Hanna, supra), and in light of the high price of soybean oil-derived biodiesel relative to petrodiesel at the present time, extending or replacing soybean oil feedstock with the much cheaper tallow would be advantageous. A major drawback in the use of neat tallow esters, however, is their cold temperature properties when compared to soy or petroleum diesel fuel. The search has thus continued for methods to effectively utilize cheaper feedstocks in an economically feasible means of producing biofuel and lubricant alternatives or additives.

SUMMARY OF THE INVENTION

We have discovered a novel process for the preparation of alkyl esters that are useful biofuels, lubricants or additives to biofuels or lubricants.

In accordance with this discovery, it is an object of the invention to provide a method for the preparation of alkyl esters by the lipase-catalyzed transesterification of alcohols to synthesize normal and branched chain alkyl esters using vegetable oils, tallow and restaurant grease as substrates.

Other objects and advantages will be readily apparent from the following description.

DETAILED DESCRIPTION OF THE INVENTION

Figure 1:
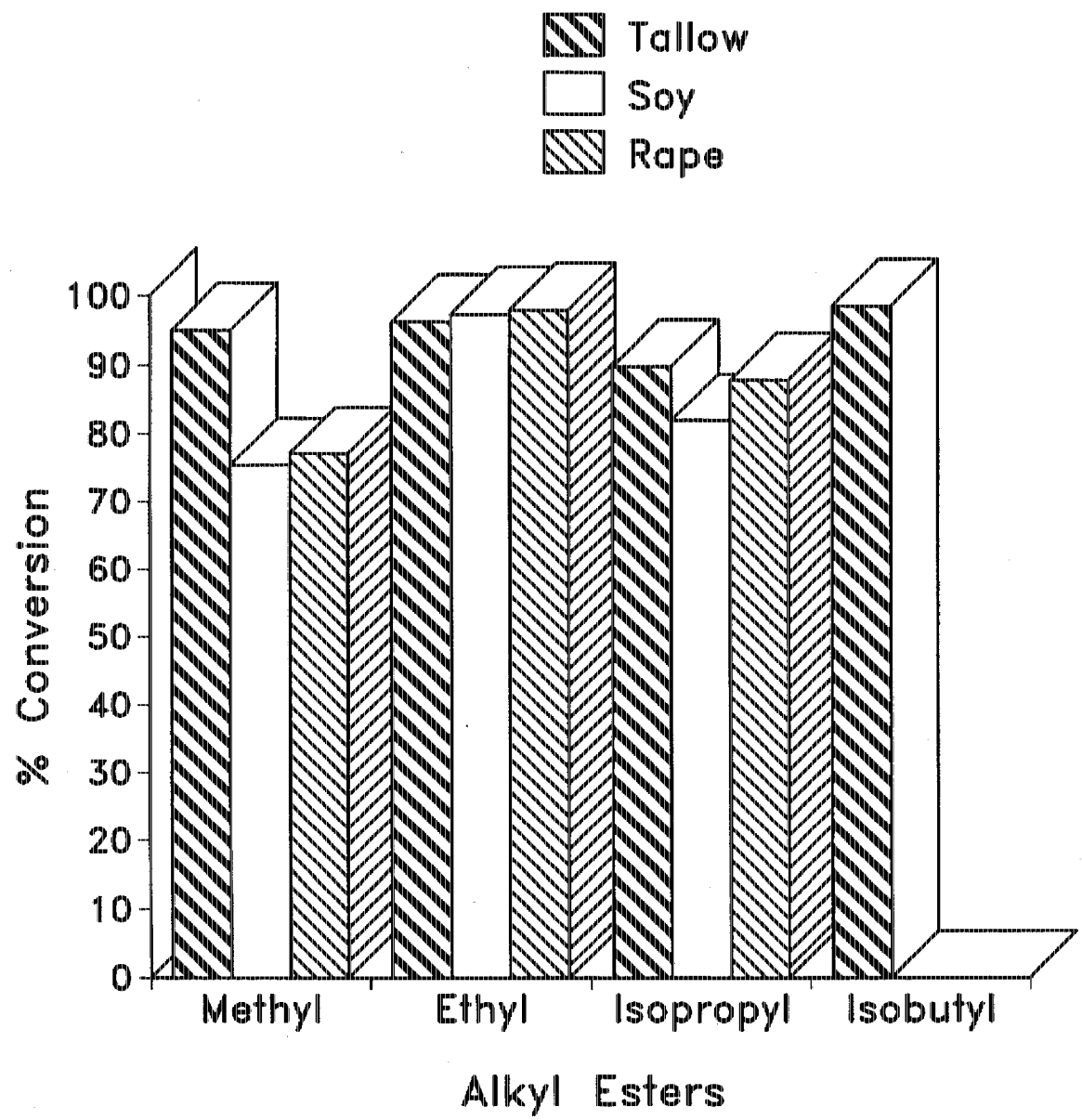
FIG. 1 shows the lipase-catalyzed transesterification of fats and oils with primary (*Mucor miehei* lipase) and secondary (*Candida antarctica* lipase) alcohols.

Studies were carried out to evaluate the activities of several commercially available lipases having varied specificities in the transesterification reaction. Using either hexane or petroleum ether as solvent under conditions described by Mittelbach (supra), the lipases were screened for their ability to transesterify the triglycerides of olive oil, soybean oil and tallow with short chain primary alcohols to their alkyl ester derivatives. The enzymes studied included 1,3-specific (*Mucor miehei* and *Rhizopus delemar*), as described by McNeill and Sonnet (1995. *J. Am. Oil Chem. Soc.* vol. 72, pp. 213–218), acyl-specific (*Geotrichum candidum*), as described by K. D. Mukherjee (1990. *Biocatalysis.* vol. 3, pp. 277–293) and nonspecific (*Candida antarctica* and *Pseudomonas cepacia*), as described by McNeill and Sonnet (supra), lipases. Results of the studies are shown in Table 1.

With methanol, the lipase from *M. miehei* (Lipozyme™ IM60) was the most effective in converting tallow to the respective alkyl esters (Table 1), and it was found to be the most efficient for the transesterification of triglycerides with primary alcohols to alkyl esters for the homologous series methanol to 1-butanol and isobutanol. In addition, transesterifications with methanol and ethanol were observed to be sensitive to water added to the reaction mixtures, with water greatly reducing the amount of ester formed. The use of 95% ethanol instead of absolute ethanol, for example, gave poorer conversion to ester (Table 1), with conversions dropping from 98% to 68%.

TABLE 1

Lipase-Catalyzed Transesterification of Triglycerides to Alkyl Esters with Primary Alcohols[a]

| Substrate | Alcohol | Lipase | Temp. (°C.) | % Composition of product[b,c] | | | |
|---|---|---|---|---|---|---|---|
| | | | | MG | DG | TG | Ester |
| Tallow | Methanol | M. miehei[d] | 45 | 0.5 e | 8.2 e | 13.6 f | 77.8 b |
| Tallow[e] | Methanol | M. miehei | 45 | 0.1 e | 3.5 f-j | 1.5 g | 94.8 a |
| Soybean | Methanol | M. miehei | 45 | 1.4 e | 12.5 d | 10.7 f | 75.4 b,c |
| Rape | Methanol | M. miehei | 45 | 1.9 d,e | 7.8 e,f | 13.0 f | 77.3 b |
| Tallow | Methanol | C. antarctica[d] | 45 | 5.1 c | 12.8 d | 53.5 d | 25.7 d |
| Tallow | Methanol | P. cepacia | 45 | 0.0 e | 6.9 e,f,g | 79.2 b | 13.9 e,f |
| Soybean | Methanol | P. cepacia | 45 | 2.4 d,e | 17.8 c | 65.3 c | 14.5 e,f |
| Olive | Methanol | P. cepacia | 45 | 1.3 e | 24.2 a,b | 50.1 d | 24.4 d |
| Tallow | Methanol | R. delemar | 45 | 0.2 e | 4.1 e-i | 95.0 a | 0.8 g |
| Olive | Methanol | R. delemar | 45 | 0.2 e | 3.1 g,h,i | 96.1 a | 0.6 g |
| Soybean | Methanol | R. delemar | 45 | 0.2 e | 3.9 e-i | 95.0 a | 0.8 g |
| Tallow | Methanol | G. candidum | 45 | 6.3 c | 3.7 f-i | 77.5 b | 12.5 e,f |
| Tallow | Ethanol | M. miehei | 45 | 0.1 e | 0.9 h,i | 0.7 g | 98.3 a |
| Tallow | Ethanol[f] | M. miehei | 45 | 14.4 b | 22.4 b | 1.6 g | 68.0 f,g |
| Tallow | Ethanol | M. miehei | 35 | 0.0 e | 4.6 e-h | 1.4 g | 93.9 a |
| Tallow | Ethanol | M. miehei | 55 | 0.4 e | 3.3 g,h,i | 1.8 g | 94.5 a |
| Soybean | Ethanol | M. miehei | 45 | 0.6 e | 1.2 h,i | 0.8 g | 97.4 a |
| Rape | Ethanol | M. miehei | 45 | 0.8 e | 0.3 h,i | 0.3 g | 98.2 a |
| Tallow | Ethanol | P. cepacia | 45 | 17.6 a | 15.7 c,d | 52.7 d | 13.7 e,f |
| Tallow | Ethanol | R. delemar | 45 | 4.3 c,d | 28.5 a | 46.0 d,e | 21.2 d,e |
| Tallow | Propanol | M. miehei | 45 | 0.2 e | 1.5 h,i | 0.1 g | 98.3 a |
| Tallow | Propanol[f] | M. miehei | 45 | 0.7 e | 0.5 h,i | 0.3 g | 98.6 a |
| Tallow | Butanol | M. miehei | 45 | 0.1 e | 0.1 i | 0.2 g | 99.6 a |
| Tallow | Butanol[f] | M. miehei | 45 | 0.6 e | 0.5 h,i | 0.8 g | 98.1 a |
| Tallow | Isobutanol | M. miehei | 45 | 0.1 e | 0.8 h,i | 0.8 g | 98.5 a |
| Tallow | Isobutanol[f] | M. miehei | 45 | 0.2 e | 0.2 i | 0.2 g | 99.4 a |
| Tallow | Isobutanol | P. cepacia | 45 | 6.8 c | 27.1 a | 37.3 e | 28.8 d |
| Tallow | Isobutanol | R. delemar | 45 | 0.6 e | 16.3 c,d | 72.7 b,c | 10.4 f |

[a]Reaction conditions for transesterification were as follows: 0.34M triglyceride in hexane (8-mL), 200 rpm, 5 h reaction time.
[b]Determined by gas chromatography.
[c]Means (n = 3) in the same column with no letter in common are significantly different (p < 0.05) by Bonferroni LSD.
[d]M. miehei IM60, C. antartica SP435.
[e]Reaction time was 8 h.
[f]Water, 6.0 mol % based on triglyceride, was added to reaction.

A mixture of alcohol (methanol, ethanol, 1-propanol, 1-butanol or isobutanol) and tallow (3:1 molar ratio) was reacted in hexane in the presence of enzyme (12.5% based on weight of tallow). Water did not appear to affect ester production in these instances, and the conversions were practically constant over temperature ranges between 35°–55° C., as exemplified by the ethanolysis of tallow (Table 1).

Transesterification of secondary alcohols in hexane showed a completely different trend (Table 2): the lipases from C. antarctica (SP435) and P. cepacia (PS30) gave higher ester conversions than M. miehei (IM60). Enzyme concentration was 25 wt % based on weight triglyceride. Reactions run without the addition of water were sluggish for both the SP 435 and PS30 lipases. In both cases a maximum conversion of 23–30% was obtained overnight (16 hr). The addition of small amounts of water (3–100 μl, or about 6 mol % of triglyceride) improved conversions. The need for the presence of water was supported by the ease with which high free fatty acid-containing greases were converted to their corresponding branched alkyl esters. The opposite effect was observed in the case of methanol, which was extremely sensitive to the presence of water. For branched chain alcohols, better conversions were obtained when the reactions were run neat, as seen with isopropanol and 2-butanol (Table 3). Lowered yields when using the normal alcohols, methanol and ethanol, in solvent-free reactions were observed and could be attributed to unfavorable viscosity conditions, which affected mixing of substrates with the lipase.

TABLE 2

Lipase-Catalyzed Transesterification of Tallow to Alkyl Esters with Secondary Alcohols[a]

| Alcohol | Solvent | Lipase | Time (h) | % Composition of Products[b,c] | | | |
|---|---|---|---|---|---|---|---|
| | | | | MG | DG | TG | Ester |
| Isopropanol | Hexane | C. antarctica[d] | 5 | 0.8 b | 8.7 d | 49.3 b | 41.2 d |
| Isopropanol | Hexane | P. cepacia | 5 | 5.2 a | 24.7 b | 26.0 c | 44.1 4 |
| Isopropanol | Hexane | M. miehei[d] | 5 | 7.4 a | 14.3 c | 54.0 b | 24.3 e |
| Isopropanol | Hexane[e] | C. antarctica | 5 | 2.1 b | 5.2 d,e | 31.5 c | 61.2 b |
| Isopropanol | Hexane | C. antarctica | 16 | 0.0 b | 1.1 f | 47.2 b | 51.7 c |

TABLE 2-continued

Lipase-Catalyzed Transesterification of Tallow to Alkyl Esters with Secondary Alcohols[a]

| | | | | % Composition of Products[b,c] | | | |
|---|---|---|---|---|---|---|---|
| Alcohol | Solvent | Lipase | Time (h) | MG | DG | TG | Ester |
| 2-Butanol | Hexane | C. antarctica | 5 | 0.2 b | 1.9 e,f | 74.2 a | 23.7 e |
| 2-Butanol | Hexane | P. cepacia | 5 | 0.3 b | 29.7 a | 29.0 c | 41.0 d |
| 2-Butanol | Hexane | M. miehei | 5 | 2.4 b | 23.2 b | 54.3 b | 19.6 e |
| 2-Butanol | Hexane[e] | C. antarctica | 5 | 6.2 a | 8.3 d | 49.6 b | 39.0 d |
| 2-Butanol | Hexane | C. antarctica | 16 | 0.0 b | 1.1 f | 15.4 d | 83.8 a |

[a]Reaction conditions were as follows: 0.34M tallow in hexane (8 mL), 45° C., 0.3 g of enzyme, 200 rpm.
[b]Determined by gas chromatography.
[c]Means (n = 3) in the same column with no letter in common are different (p < 0.05) by Bonferroni LSD.
[d]M. miehei IM60, C. antartica SP435.
[e]water added at 6 mole % based on tallow.

Figure 2:
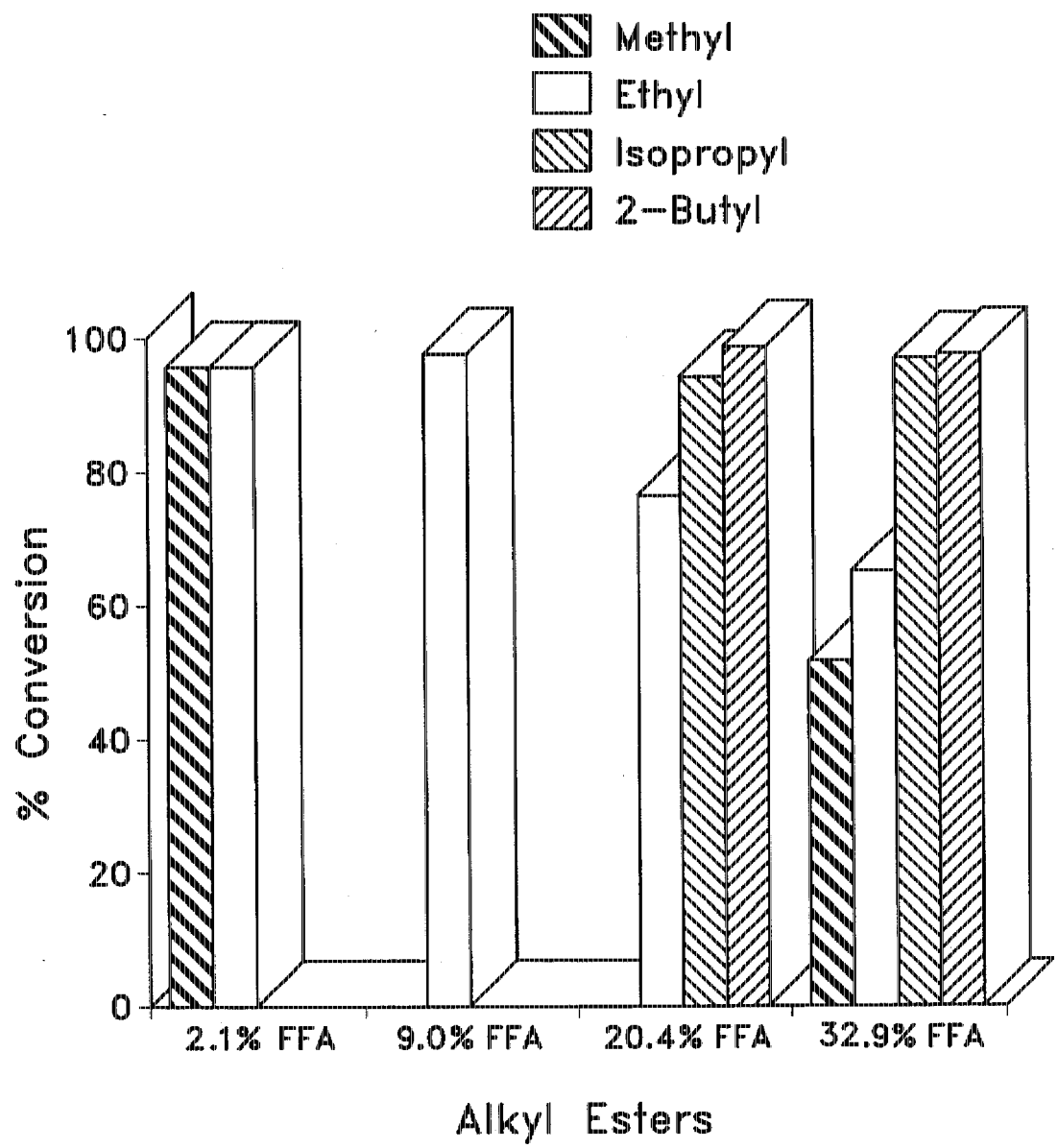
FIG. 2 shows the enzymatic transesterification and esterification of free fatty acid (FFA)-containing triglyceride feedstocks using *M. miehei* (primary alcohols) and *C. antarctica* (secondary alcohols) lipases.

The conditions utilized for tallow (0.34M tallow in hexane, 45° C., 300 rpm, 4-8 hr, 12.5-25% enzyme by weight of tallow, neat in the case of branched alcohols) have been used to scale up reactions involving the primary alcohols to give over 95% conversions and over 90% for secondary alcohols with very minimum production of the other glycerides (Table 3). These conditions also gave conversions between 75-95% when applied to soybean and rapeseed oils, as exemplified by methanolysis, ethanolysis and isopropanolysis reactions (FIG. 1). When applied to greases with varying fatty acid contents, methanolysis was curtailed for feedstocks where the free fatty acid content was greater than 9% while ethanolysis was effective below 22.4% FFA. Secondary alcohols, on the other hand, were extremely effective in converting high FFA-containing feedstocks to their respective alkyl esters (FIG. 2). This is in agreement with the observation that water appears to retard the conversion to ester when methanol is the substrate but does promote ester formation when secondary alcohols are used with C. antarctica as the lipase.

transesterification of triglyceride-containing substances to form alkyl esters may be carried out according to the following procedure: a triglyceride-containing substance is combined with an alcohol and a lipase (with or without solvent) to form a reaction mixture. The mixture is shaken for an amount of time and at a temperature effective for transesterification to occur. Optionally, a small amount of water may be added to the mixture. When the reaction is complete, the alkyl ester products are separated from the residual reaction mixture by conventional methods such as filtration of the enzyme and removal of solvent if present.

Useful triglyceride- and free fatty acid-containing substances are tallow, vegetable oils, greases, other animal fats and rendered fats and oils. Preferred are tallow and greases. If necessary, the substance may be dissolved in an organic solvent before combining with alcohol and enzyme. Effective organic solvents are hexane, petroleum ether, isooctane and other alkanes and arenes or chlorinated solvents. Preferred solvents are hexane and petroleum ether. The amount of solvent required is not critical and is used only to improve miscibility of the reactants.

TABLE 3

Lipase-Catalyzed Transesterification of Tallow with Alcohols[a]

| | | | | % Composition of products[b,c] | | | |
|---|---|---|---|---|---|---|---|
| Alcohol | Solvent | Lipase | Time (hr) | MG | DG | TG | Ester |
| Methanol | Hexane | M. miehei[d] | 5 | 0.5 c,d | 8.2 b | 13.6 d | 73.8 d |
| Methanol | Hexane | M. miehei | 8 | 0.1 d | 3.5 c | 1.5 e | 94.8 a |
| Methanol | none[e] | M. miehei | 8 | 5.2 a | 10.0 a | 67.6 a | 19.4 g |
| Ethanol | Hexane | M. miehei | 5 | 0.2 d | 1.2 d | 0.6 e | 98.5 a |
| Ethanol | none[e] | M. miehei | 5 | 1.8 b,c | 3.7 c | 29.0 c | 65.5 e |
| Isopropanol | Hexane | C. antartica | 16 | 0.0 d | 1.1 d | 47.2 b | 51.7 f |
| Isopropanol | none[e] | C. antartica[d] | 16 | 2.2 b | 7.0 b | 0.9 e | 90.3 b |
| Isobutanol | Hexane | M. miehei | 5 | 0.1 d | 0.8 d | 0.6 e | 98.5 a |
| Isobutanol | none[e] | M. miehei | 5 | 0.8 c,d | 0.9 d | 1.0 e | 97.4 a |
| 2-Butanol | Hexane | C. antarctica | 16 | 0.0 d | 1.1 d | 15.4 d | 83.8 c |
| 2-Butanol | none[e] | C. antarctica | 16 | 1.3 b,c,d | 1.3 d | 1.0 e | 96.4 a |

[a]Reaction condition for transesterification were as follows: 0.34M tallow in hexane (8 mL), 45° C., 200 rpm.
[b]Determined by gas chromatography.
[c]Means (n = 3) in the same column with no letter in common are significantly different (p < 0.05) by Bonferroni LSD.
[d]M. miehei IM60, C. antartica SP435.
[e]Reaction conditions the same except no solvent used.

Lipase esterification is thus a viable method for the production of alkyl esters from triglyceride feedstocks such as tallow, vegetable oil and FFA-containing greases. The Both primary (normal and branched) and secondary alcohols may be utilized in the process. When secondary alcohols are utilized, it is preferred to add water in amounts ranging from about 0 to about 6 mol % of the triglyceride. Useful primary alcohols are ethanol and isobutanol, and useful secondary alcohols are isopropanol and 2-butanol. They may be present in amounts ranging from about 3 to about 10 moles/1 mole triglyceride.

Time and temperature ranges are dependent upon the lipase selected and the degree of conversion acceptable. These parameters are easily obtained experimentally by following the procedures set forth in the specific example. In general, from about 4- to about 16-hr reaction times and temperatures ranging from about 30° to about 60° C. are useful.

While the process has been exemplified in terms of the lipases discussed, any effective lipase may be utilized, and, since lipase specificities are generally available, it is within the level of skill in the art to carry out the experimentation described herein in order to select the appropriate enzyme. Factors to consider are specificity, substrates and the intended end product. In general, specificity of the enzyme is selected depending on the desired end product. However, it has been found that non-specific enzymes are particularly useful in the production of alkyl esters for use in biofuels and lubricants. *P. cepacia* and *C. antarctica*, for example, were found to be very effective when used with 2-propanol and 2-butanol in the transesterification of beef tallow, vegetable oil and greases, resulting in greater than 90% conversions.

In order to achieve improvement in the cold temperature properties of tallow esters, blending the tallow esters with soy esters is effective. In addition, utilizing higher molecular weight alcohols (i.e., higher than methanol) in the reaction results in improved cold temperature properties. For example isopropyl and 2-butyl esters have better cold temperature properties than the corresponding methyl and ethyl esters of triglycerides and are better diesel fuel alternatives, either neat or blended with diesel. The branched alkyl esters of tallow and greases, unlike the methyl ester counterparts, have cold temperature properties similar to existing biofuels.

The lipase-catalyzed transesterification is more efficient than the chemical approach and has the added advantages of easily-recoverable glycerol, minimal waste residues, recycling of catalyst, the use of high fatty acid-containing feedstocks, low reaction temperatures and high conversions to alkyl esters. Moreover, the conversion of triglycerides to branched esters is particularly rapid, an important factor when considering tallow as a feedstock due to the improved low-temperature properties of the branched esters of tallow, and feedstocks having a high content of free fatty acids, such as restaurant grease, are easily converted.

EXAMPLES

Example 1: Transesterification Reaction

Screening experiments were conducted at 10% lipase by weight of triglyceride with hexane as solvent. The reaction was run as follows: to a stoppered 125-ml Erlenmeyer flask containing substrate was added 3 mole equivalenty of the alcohol with the appropriate amount of enzyme. The reaction mixture was shaken at 200 rpm for 5 hr at 45° C. The progress of the reaction was followed by taking 100-μl aliquots at selected time intervals, concentrating to a residue which was derivatized with N,O-(bis-trimethylsilyl) trifluoroacetamide (BSTFA) for gas chromatographic analysis. Substrates utilized were tallow (Chemol Corp., Greensboro, N.C.), high free fatty acid-containing greases ("restaurant" or "yellow", Kaluzny Bros. Joliet, Ill.), rapeseed oil (Calgene Chemical, Skokie, Ill.) and soybean and olive oil (purchased from a local supermarket). Enzymes utilized were supported lipases *M. miehei* (Lipozyme™ IM20/60) and *C. antarctica* (SP435), both obtained from Novo Nordisk (Franklinton, N.C.). Lipase powders were from *G. candidum*, *P. cepacia* (both from Amano Pharmaceutical, Troy, Va.) and *R. delemar* (Seikagaku Kogyo Co., Tokyo, Japan).

Example 2: Analysis of Products

For solvent reactions, an aliquot was taken at selected time intervals and freed of solvent under a stream of nitrogen at 45° C. A portion of the residue (10 mg) was dissolved in tetrahydrofuran (100 μl) and BSTFA (200 ul) was added. The mixture was heated on a water bath at 90°–95° C. for 15 min. After cooling to room temperature, hexane (5 ml) was added. An aliquot of 0.5 μl of the mixture was analyzed by gas chromatography as follows: a 15 m long, non-polar high temperature capillary column (DB1-HT), i.d. 0.32 mm, film thickness 0.1 micron, was used (J&W Scientific, Folson, Calif.) for analysis. The samples were injected directly on-column using a Hewlett Packard 5890 gas chromatograph, helium carrier gas flow rate of 5.5 ml/min, flame ionization detection with an initial oven temperature of 70° C. followed by a temperature program of 20° C./min to final temperature of 350° C., which was held for 4 min. Peaks in the chromatograms were identified by comparison of retention times with standards of known composition. All solvents were high-performance liquid chromatography (HPLC) grade and were purchased from Burdick and Jackson (Muskegon, Mich.). BSTFA was obtained from Regis Chemical Co. (Morton Grove, Ill.). Unless otherwise stated, all other chemicals were from Aldrich Chemical Co. (Milwaukee, Wis.).

We claim:

1. A method of producing alkyl esters useful as biofuels and lubricants from triglyceride- or free fatty acid-containing substances, said method comprising
   a) dissolving said triglyceride- or free fatty acid-containing substance in an organic solvent,
   b) combining the dissolved triglyceride- or free fatty acid-containing substance with an alcohol and a lipase to form a reaction mixture,
   c) incubating the reaction mixture for a time and at a temperature sufficient for transesterification between the triglyceride or esterification between the free fatty acid and the alcohol to occur,
   d) separating the alkyl esters from the reaction mixture.

2. The method of claim 1, wherein the triglyceride- or free fatty acid-containing substance is selected from the group consisting of tallow, vegetable oils, greases, animal fats and rendered fats and oils.

3. The method of claim 2, wherein the triglyceride- or free fatty acid-containing substance is tallow or grease.

4. The method of claim 1, wherein said alcohol is ethanol, propanol, isopropanol, 1-butanol, 2-butanol or isobutanol.

5. The method of claim 1, wherein said alcohol is a secondary alcohol and water is present in the reaction mixture.

6. The method of claim 5, wherein water is present in the reaction mixture in an amount up to about 6 mol % of the triglyceride- or free fatty acid-containing substance.

7. The method of claim 1, wherein alcohol is present in the reaction mixture in an amount from about 3 to about 10 moles per 1 mole triglyceride- or free fatty acid-containing substance.

8. The method of claim 1, wherein said organic solvent is an alkane, arene, chlorinated solvent or petroleum ether.

9. The method of claim 8, wherein said organic solvent is hexane, petroleum ether, isooctane.

10. The method of claim 9, wherein said organic solvent is hexane or petroleum ether.

11. The method of claim 1, wherein the lipase is from *Mucor miehei* or from *Candida antarctica*.

12. The method of claim 1, wherein said reaction mixture is incubated from about 4 to about 16 hours.

13. The method of claim 1, wherein said reaction mixture is incubated at a temperature of about 30° C. to about 60° C.

* * * * *